United States Patent [19]

Bastart et al.

[11] Patent Number: 5,750,561
[45] Date of Patent: *May 12, 1998

[54] COMPOSITIONS CONTAINING TAXANE DERIVATIVES

[75] Inventors: Jean-Pierre Bastart, Lesigny; Thierry Dupechez, Villemoisson Sur Orge; Jean-Louis Fabre, Paris, all of France

[73] Assignee: Rhone-Poulenc Rorer, S.A., Antony Cedex, France

[*] Notice: The term of this patent shall not extend beyond the expiration date of Pat. No. 5,403,858.

[21] Appl. No.: 422,672

[22] Filed: Apr. 12, 1995

Related U.S. Application Data

[63] Continuation of Ser. No. 930,393, Aug. 4, 1993, abandoned.

[30] Foreign Application Priority Data

Jul. 8, 1991 [FR] France .................................. 9108527

[51] Int. Cl.⁶ ...................... A61K 31/335; A61K 31/34; A61K 9/50
[52] U.S. Cl. ...................... 514/449; 514/471; 514/408; 424/502
[58] Field of Search ................... 514/449, 471, 514/408; 424/502

[56] References Cited

U.S. PATENT DOCUMENTS

| | | | |
|---|---|---|---|
| 4,206,221 | 6/1980 | Miller et al. | 424/278 |
| 4,814,470 | 3/1989 | Colin et al. | 514/449 |
| 4,960,790 | 10/1990 | Stella et al. | 514/449 |
| 5,403,858 | 4/1995 | Bastard et al. | 514/449 |

OTHER PUBLICATIONS

Merck Index, 11th Ed., #7559, (1989), p. 1207.
C.A. 106 (22): 182581c—Tarr et al. (1987).

*Primary Examiner*—Theodore J. Criares
*Attorney, Agent, or Firm*—Finnegan, Henderson, Farabow, Garrett & Dunner, L.L.P.

[57] ABSTRACT

The invention provides new compositions containing taxane derivatives, consisting of solutions of such derivatives in a solvent mixture composed of ethanol and polysorbate. These compositions are used to prepare perfusions.

11 Claims, No Drawings

COMPOSITIONS CONTAINING TAXANE DERIVATIVES

This is a continuation of application Ser. No. 07/930,393, filed on Aug. 4, 1993, now abandoned.

The present invention relates to compositions containing therapeutic agents having antitumour and antileukaemic activity. It relates more especially to pharmaceutical, and in particular injectable, dosage forms containing taxane derivatives, such as, in particular, taxol or one of its analogues or derivatives of the following general formula:

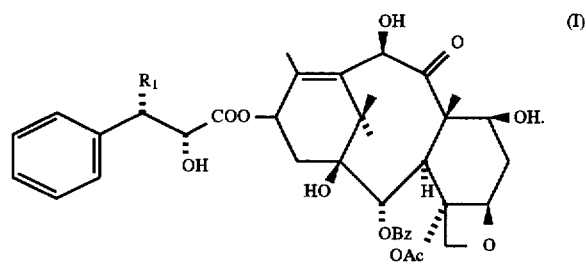

Wherein R represents a hydrogen atom or an acetyl radical and $R_1$ represents a tert-butoxycarbonylamino or benzoylamino radical. The two derivatives in which R represents an acetyl group and $R_1$ a benzoylamino group or in which R represents a hydrogen atom and $R_1$ a tert-butoxycarbonylamino radical are preferred. The first of these two compounds is better known by the name of taxol, and the second is known by the name of Taxotere.

These products exhibit in vivo substantial activity against malignant tumours, which has enabled them to be studied in the treatment of diseases resistant to other anticancer therapies.

Unfortunately, these products possess such low solubility in water that it has been necessary to prepare a formulation for an injectable preparation based on surfactant and ethanol. Ethanol is the best solvent for dissolving compounds of the formula (I).

As an example, according to the publication by Rowinsky, Lorraine, Cazenave and Donehower which appeared in the Journal of the National Cancer Institute, vol. 82, No. 15, pages 1247–1259 on 1st Aug. 1990, a first solution, termed "stock solution", containing approximately 6 mg/ml of taxol in a solvent mixture composed of:

50% by volume of ethanol
50% by volume of Cremophor EL, is prepared. For injection, this solution is mixed with a perfusion fluid containing sodium chloride or dextrose. To obtain a mixture which is stable from both a physical standpoint and a chemical standpoint, the authors of this paper state that it is necessary to limit the concentration of active principle in the perfusion solution to concentrations of approximately 0.03 to 0.6 mg/ml (see above publication, page 1251, column 1, third paragraph).

Now, it is desirable to be able to inject sufficient doses of active principle; to this end, clinicians would like to inject concentrations of active principle of between approximately 0.3 and 1 mg/ml in the perfusion fluid; above these doses, anaphylactic shock phenomena which are difficult to control, due in the main to the Cremophor, are seen (see the publication by Rowinsky, page 1250, second column, last paragraph).

This publication also discloses that, to obtain such concentrations (between 0.3 and 1 mg/ml), it is necessary to inject solutions containing, as well as the active principle, concentrations of each of the following compounds, ethanol and most especially Cremophor, of approximately 8 g per 100 ml of solution. Since the treatment often requires the administration of high doses of active principle, and since the concentration of the active principle in the solution is relatively low, the injection of a large volume has the effect of causing, in addition to anaphylactic manifestations, manifestations of alcohol intoxication during the treatment.

It has been discovered that, by the use of the pharmaceutical dosage forms of the present invention, it is possible to avoid the use of Cremophor and greatly to reduce the ethanol concentrations used.

For this purpose, a stock solution is prepared, containing the active principle of formula I in a solvent mixture composed of ethanol, which is the best biocompatible solvent for active principles of this class, and a polysorbate surfactant, e.g. as marketed, in particular, under the name "Tween".

The stock solution is prepared by dissolving the active principle in ethanol and then gradually adding the surfactant. Solutions containing 10 to 100 mg/ml of active principle in a mixture containing approximately 50% of surfactant can be prepared in this manner.

The present invention then makes it possible to replace the Cremophor, described in the publication of the Journal of National Cancer Institute, by a polysorbate. In effect, when an injectable solution containing ethanol and a polysorbate 80 surfactant in place of Cremophor was used in the clinical situation, it became apparent that the anaphylactic reactions were greatly reduced compared with the use of the same solution prepared with Cremophor. In addition to this considerable advantage, it became apparent, most surprisingly, that, in the bottles of stock solution, the concentration of active principle can reach 15 mg/ml. The perfusion fluid after dilution of these bottles contains an amount of ethanol, and also an amount of surfactant, which is reduced a little over twofold.

The perfusions prepared from the above stock solutions, and containing a concentration of active principle of, e.g., 1 mg/ml, which is a preference, or less, contain less than 50 ml/l and preferably less than 35 ml/l of surfactant and of ethanol, which represents a reduction of approximately 40% relative to the perfusions of the prior art.

The new perfusions are stable from a physical standpoint, that is to say no precipitation phenomenon is seen to appear within approximately 8 hours.

The taxol or Taxotere perfusions may be injected into humans at a predetermined flow rate depending on the amount of active principle it is desired to inject. The anaphylactic shock phenomena which were observed with the solutions of the prior art are not observed with these solutions.

The invention is described more completely in the Examples which follow, which are not to be considered as limiting the invention.

EXAMPLES ACCORDING TO THE INVENTION

EXAMPLE 1

Taxotere (0.450 g) is dissolved in ethanol (15 ml). The mixture is made to 30 ml with polysorbate 80 to obtain a solution containing Taxotere (15 mg/ml). The physicochemical stability of this solution is satisfactory.

After mixing with a 5% glucose solution so as to obtain a final concentration of 1 mg/ml, this solution contains 33 ml/l of polysorbate 80 and 33 ml/l of ethanol.

The perfusion is stable for more than 21 hours, i.e. no precipitation phenomenon is seen during this period.

EXAMPLE 2

Example 1 is reproduced with an initial concentration of 10 mg/ml of Taxotere; the results are shown in Table 1.

COMPARATIVE EXAMPLE ACCORDING TO THE PRIOR ART

Taxol (0.180 g) is dissolved in ethanol (15 ml). The mixture is made to volume with Cremophor to obtain a solution (30 ml) which contains taxol (6 mg/ml).

This solution is diluted in the same perfusion solution as above to five a final concentration of 1 mg/ml; the perfusion solution contains 87.7 ml/l of Cremophor and 87.7 ml/l of ethanol. The perfusion solution is stable for more than 21 hours.

EXAMPLE 3

Taxotere (65 g) is dissolved in ethanol (2083 ml). The volume is adjusted to 4147 ml by adding polysorbate 80 (2083 ml). The mixture is homogenised by mechanical stirring. It is filtered through a filter of pore size 0.2 μm. A solution containing Taxotere (approximately 15 mg/ml) is obtained.

After dilution to a Taxotere content of 1 mg/ml in a perfusion bag containing 5% dextrose, this solution is stable for at least 96 hours.

5. A perfusion, which contains approximately 1 mg/ml or less of compound of formula as defined in claim 1, and which contains less than 35 ml/l of ethanol and less than 35 ml/l of polysorbate, wherein said perfusion is capable of being injected without anaphylactic or alcohol intoxication manifestations being associated therewith.

6. A stock solution consisting essentially of a mixture of taxotere and ethanol in a ratio of about 3:100 by weight, and an amount of polysorbate to provide a solution containing about 10 to 15 mg/ml of taxotere, whereby said stock solution is used to form an injectable solution which contains up to about 1 mg/ml of the compound of formula as defined in claim 1, said injectable solution being capable of being injected without anaphylactic or alcohol intoxication manifestations being associated herewith.

7. A perfusion consisting essentially of the stock solution of claim 6 and an amount of glucose solution or dextrose solution to obtain a solution containing about 1 mg/ml of taxotere.

8. A therapeutic composition consisting essentially of a taxane derivative dissolved in a mixture of ethanol and a polysorbate, whereby said therapeutic composition forms or is used to form an injectable solution which contains up to about 1 mg/ml of the compound of formula as defined in claim 1, said injectable solution being capable of being injected without anaphylactic or alcohol intoxication manifestations being associated herewith.

9. The composition of claim 8 wherein said taxane derivative is taxol or an analogue or derivative thereof.

TABLE 1

| Example | Product | Solvent | Stock solution concentration | Active principle in the perfusion | Surfactant in the perfusion | Ethanol in the perfusion | Stability |
|---|---|---|---|---|---|---|---|
| Comparative | taxol | EtOH/Crem | 6 mg/ml | 1 mg/ml | 87.7 ml/l | 87.7 ml/l | >21 H |
|  | taxol | EtOH/Poly | 6 mg/ml | 1 mg/ml | 83.3 ml/l | 83.3 ml/l | >21 H |
| 1 | Taxotere | EtOH/Poly | 15 mg/ml | 1 mg/ml | 33.3 ml/l | 33.3 ml/l | >21 H |
| 2 | Taxotere | EtOH/Poly | 10 mg/ml | 1 mg/ml | 50 ml/l | 50 ml/l | >21 H |

We claim:

1. A composition consisting essentially of a compound of formula:

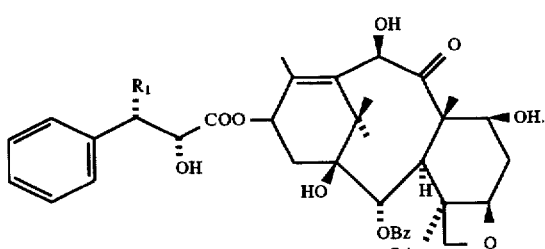

in which R represents a hydrogen atom or an acetyl radical and $R_1$ represents a tert-butoxycarbonylamino or benzoylamino radical, dissolved in a mixture of ethanol and a polysorbate whereby said composition is used to form an injectable solution which contains up to about 1 mg/ml of the compound of formula I, said injectable solution being capable of being injected without anaphylactic or alcohol intoxication manifestations being associated therewith.

2. A composition according to claim 1, wherein, in the compound of formula (I), R represents a hydrogen atom and $R_1$ represents a tert-butoxycarbonylamino radical.

3. A composition according to claim 1, wherein, in the compound of formula (I), R represents an acetyl group and $R_1$ represents a benzoylamino radical.

4. A composition according to claim 1, which contains between 6 and 15 mg/ml of compound of formula (I).

10. The composition of claim 8 wherein said taxane derivative is taxotere or an analogue or derivative thereof.

11. A composition consisting essentially of a compound of formula

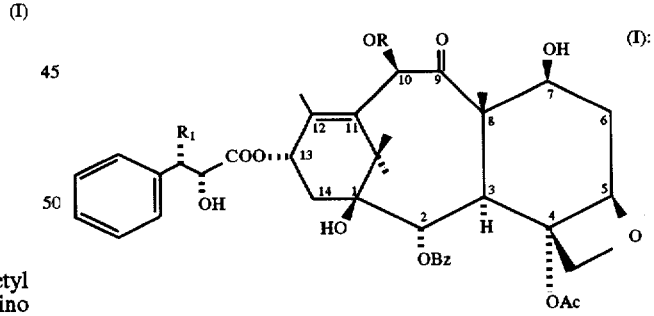

in which R represents a hydrogen atom or an acetyl radical and $R_1$ represents a tert-butoxycarbonylamino or benzoylamino radical, dissolved in a mixture of ethanol and polysorbate, wherein said ethanol is present in an amount of less than 5% and said polysorbate is present in an amount of less than 5%, said composition being used to form an injectable solution capable of being injected without anaphylactic or alcohol intoxication manifestations being associated herewith.

* * * * *

UNITED STATES PATENT AND TRADEMARK OFFICE
CERTIFICATE OF CORRECTION

PATENT NO. : 5,750,561
DATED : May 12, 1998
INVENTOR(S) : BASTART et al.

It is certified that error appears in the above-indentified patent and that said Letters Patent is hereby corrected as shown below:

Claim 1, column 3, lines 43-51, in the formula (I),

" 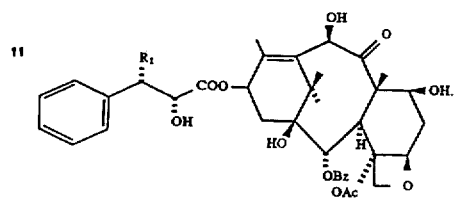 " should read -- 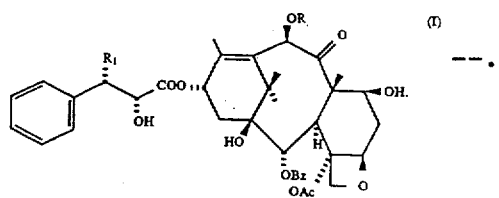 --.

Signed and Sealed this

Twenty-seventh Day of April, 1999

*Attest:*

Q. TODD DICKINSON

*Attesting Officer*   *Acting Commissioner of Patents and Trademarks*

Disclaimer 5,750,561—Jean-Pierre, Bastart, Lesigny; Thierry Dupechez, Villemoisson Sur Orge; Jean-Louis Fabre, Paris, all of France. COMPOSITIONS CONTAINING TAXANE DERIVATIVES. Patent Dated May 12, 1998. Disclaimer filed November 8, 2007 by Assignee, Aventis Pharma S.A.

The term of this patent shall not extend beyond the expiration date of Patent No. 5,698,582.

*(Official Gazette, November 24, 2009)*